United States Patent
Xiao et al.

(10) Patent No.: US 8,809,779 B2
(45) Date of Patent: Aug. 19, 2014

(54) METHOD AND SYSTEM FOR HEATING SUBSTRATE IN VACUUM ENVIRONMENT AND METHOD AND SYSTEM FOR IDENTIFYING DEFECTS ON SUBSTRATE

(75) Inventors: Hong Xiao, Pleasanton, CA (US); Yi-Xiang Wang, Fremont, CA (US)

(73) Assignee: Hermes Microvision, Inc., Hsinchu (TW)

( * ) Notice: Subject to any disclaimer, the term of this patent is extended or adjusted under 35 U.S.C. 154(b) by 440 days.

(21) Appl. No.: 12/339,558

(22) Filed: Dec. 19, 2008

(65) Prior Publication Data

US 2010/0155596 A1   Jun. 24, 2010

(51) Int. Cl.
  *G01N 23/00* (2006.01)
  *G01N 23/22* (2006.01)
  *H05B 3/00* (2006.01)
(52) U.S. Cl.
  CPC .......... *H05B 3/0047* (2013.01); *G01N 23/2202* (2013.01)
  USPC ............................ 250/307; 250/306; 250/310
(58) Field of Classification Search
  CPC .................................................... G01N 23/00
  USPC ........................................................ 250/307
  See application file for complete search history.

(56) References Cited

U.S. PATENT DOCUMENTS

| | | | |
|---|---|---|---|
| 6,445,199 B1 * | 9/2002 | Satya et al. | 324/754.21 |
| 6,971,791 B2 * | 12/2005 | Borden et al. | 374/5 |
| 2002/0190207 A1 * | 12/2002 | Levy et al. | 250/306 |

* cited by examiner

*Primary Examiner* — Phillip A Johnston
(74) *Attorney, Agent, or Firm* — WPAT, PC; Justin King

(57) ABSTRACT

A method for heating a substrate in a vacuum environment and a system therefor is provided. The system includes a chamber capable of holding the substrate located in the vacuum environment and a light source capable of projecting a light beam only on a portion of the substrate. The method includes the following steps. First, the substrate is placed in the vacuumed chamber. Thereafter, the light beam emitted from the light source is projected on the portion of the substrate, such that the portion is significantly heated before whole the substrate is heated. When the light beam is a charged particle beam projected by a charged particle beam assembly and projected on defects located on the substrate, the defects are capable of being identified by an examination result provided by an examination assembly after termination of light beam projection.

23 Claims, 4 Drawing Sheets

METHOD AND SYSTEM FOR HEATING SUBSTRATE IN VACUUM ENVIRONMENT AND METHOD AND SYSTEM FOR IDENTIFYING DEFECTS ON SUBSTRATE

FIELD OF THE INVENTION

The present invention generally relates to a method of identifying defects on a substrate and a system therefor, and more particularly to a method of identifying defects on a substrate by heating the substrate and a system therefor.

DESCRIPTION OF THE RELATED ART

Silicon wafer is a substrate material used in the fabrication of integrated circuit and other micro-devices. For maintaining the optimal yield rate of the silicon wafer, testers may use a scanning electron microscope (SEM) to inspect leakage defects, for example junction defects and short defects. However, testers can not identify the junction defects from the short defects by using the SEM directly in the prior art.

Furthermore, the silicon wafer should be heated in some fabricating processes. However, when the silicon wafer is heated, the air around the silicon wafer is also heated and the ion oscillation is induced. Therefore, some fabricating processes like using the SEM to inspect the silicon wafer may be hard to be processed. Accordingly, it is important to find a way to identify the junction defects from the short defects and to reduce the pollution induced by the ion oscillation.

SUMMARY OF THE INVENTION

The present invention is directed to a method and a system for heating only a portion of a substrate in a vacuum environment.

The present invention is also directed to a method to identify defects on a substrate.

The present invention is also directed to a system to identify defects on a substrate by using a charged particle beam.

The present invention provides a method of heating a substrate in a vacuum environment comprising the following steps. First, a substrate is placed in a vacuumed chamber. Thereafter, a light beam emitted from a light source is projected on only a portion of the substrate, such that the portion is significantly heated before the whole substrate is heated.

The present invention further provides a system for heating a substrate in a vacuum environment. The system comprises a chamber and a light source. The chamber is capable of holding a substrate located in a vacuum environment. The light source is capable of projecting a light beam only on a portion of the substrate, such that the portion is significantly heated before whole the substrate is heated.

According to an embodiment, the system further comprises at least one optical element for focusing the light beam on at least a portion of the substrate, wherein the optical element is located outside the chamber and may be selected from a group consisting of lens, mirror or combination thereof.

The present invention further provides a method for identifying defects on a substrate comprising the following steps. First, a substrate is examined by using a charged particle beam in a vacuum environment, wherein at least one defect is located on the substrate. Thereafter, a light beam emitted from a light source is projected on at least one specific defect. Next, the specific defect is examined after termination of light beam projection, such that the specific defect is identified by the examination result.

According to an embodiment, the method further comprises using at least one optical element to focus the light beam on the portion of the substrate or the defects located on the substrate, wherein the optical element is selected from a group consisting of lens, mirror or combination thereof.

The present invention further provides a system for identifying defects by using charged particle beam, wherein the system comprises a chamber, a charged particle beam assembly, a light source and an examination assembly. The chamber is capable of holding a substrate located in a vacuum environment. The charged particle beam assembly is capable of projecting a charged particle beam on the substrate. The light source is capable of projecting a light beam on at least a portion of the substrate. The examination assembly is capable of examining the substrate.

According to an embodiment, the light source is located outside the vacuum environment, for example located outside the vacuumed environment.

According to an embodiment, a power portion of the light source is located outside the vacuum environment, for example located outside the vacuumed chamber, and a luminescence portion of the light source is located inside the vacuum environment, for example located inside the vacuumed chamber.

According to an embodiment, the examination assembly is capable of controlling the charged particle beam to scan the substrate, controlling the light source to project the light beam on at least one defect located on the substrate, and examining the defect after termination of light beam projection, such that the specific defect is identified by the examination result.

According to an embodiment, the specific defect is a leakage defect.

According to an embodiment, the specific defect is identified by a gray-level temperature relation of the specific defect.

According to an embodiment, the specific defect is identified as a short defect when a gray-level of the specific defect is insensitive to the temperature of the specific defect.

According to an embodiment, the specific defect is identified as a junction defect when a gray-level of the specific defect is sensitive to the temperature of the specific defect.

According to an embodiment, the light source is selected from a group consisting of radiation lamp, laser and combination thereof.

According to an embodiment, the light source comprises a lamp, a first mirror and a second mirror. The lamp is located close to a proximal focus of the first mirror. The second mirror is located close to a distal focus of the first mirror and has a focus located on the chamber.

According to an embodiment, the configuration of the light source is adjusted such that the focus of the second mirror is located on the portion of the substrate while the substrate is located on the position to be projected by the charged particle beam.

According to an embodiment, the system further comprises a moving module for moving the substrate close to the focus of the second mirror while the focus of the second mirror is far away from the position that the substrate is projected by the charged particle beam.

According to an embodiment, the charged particle beam is an electron beam.

In the present invention, only a portion of a substrate is heated in a vacuum environment using the method or the system. Furthermore, defects on a substrate may be identified by using the method or the system of the present invention.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF THE INVENTION

Figure 1:
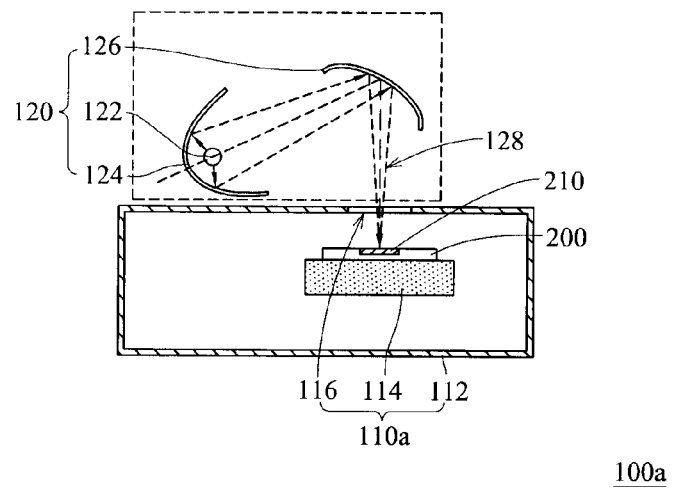
FIG. 1 is a schematic view of a system for heating a substrate in a vacuum environment according to an embodiment of the present invention.

Reference will now be made in detail to the present embodiments of the invention, example of which is illustrated in the accompanying drawings. Wherever possible, the same reference numbers are used in the drawings and the description to refer to the same or like parts.

FIG. 1 is a schematic view of a system for heating a substrate in a vacuum environment according to an embodiment of the present invention. Referring to FIG. 1, in the present embodiment, the system 100a comprises a chamber 110a and a light source 120. The chamber 110a may have a wall 112 for forming a vacuum environment and a stage 114 located in the wall 112 to hold a substrate 200. Furthermore, the light source 120 may be located outside the vacuum environment and capable of projecting a light beam 128 on a portion 210 of the substrate 200. Therefore, the system 100a can heat the portion 210 significantly in the vacuum environment before whole the substrate 200 is heated.

In more detail, the light source 120 may comprise a lamp 122, a first mirror 124 and a second mirror 126, wherein the lamp 122 may be a radiation lamp and the first mirror 124 and the second mirror 126 may be concave spherical mirrors. The lamp 122 is located close to a proximal focus of the first mirror 124, and the second mirror 126 is located close to a distal focus of the first mirror 124 and comprises a focus located on the chamber 110a. Accordingly, when the substrate 200 is placed in the chamber 110a and the portion 210 is located close to the focus of the second mirror 126, a light beam 128 emitted from the lamp 122 may be sequentially reflected by the first mirror 124 and the second mirror 126, transmitted through a window 116 of the chamber 110a located on the wall 112 and projected on only the portion 210 of the substrate 200. Therefore, the portion 210 is significantly heated in the vacuum environment before the whole substrate 200 is heated.

Figure 2A:
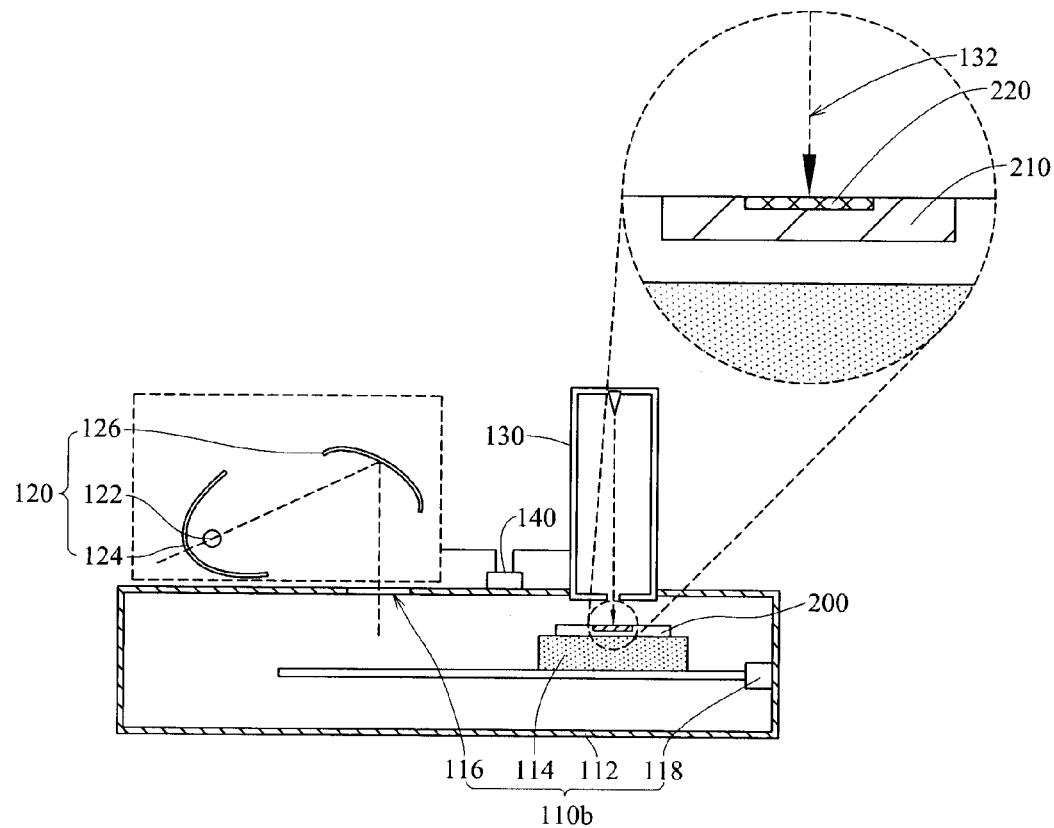
FIG. 2A is a schematic view of inspecting a substrate by using a system according to another embodiment of the present invention.
Figure 2B:
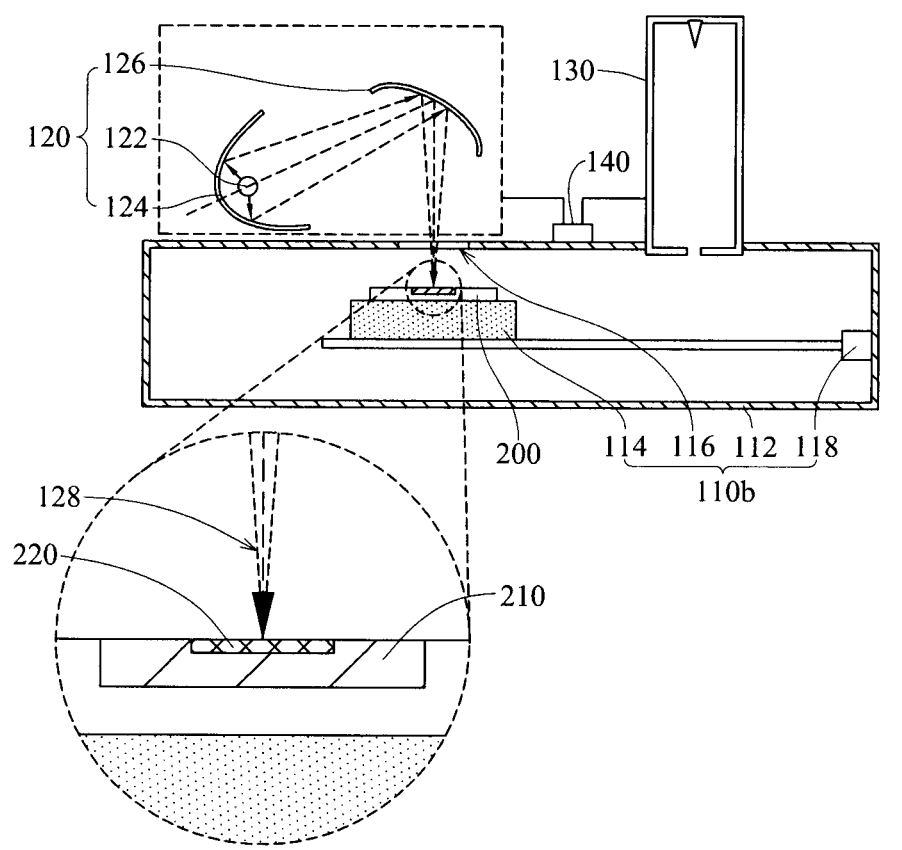
FIG. 2B is a schematic view of heating a defect on the substrate by using the system as shown in FIG. 2A.

FIG. 2A is a schematic view of inspecting a substrate by using a system according to another embodiment of the present invention. FIG. 2B is a schematic view of heating a defect on the substrate by using the system as shown in FIG. 2A. Referring to FIGS. 2A and 2B, the system 100b in the present embodiment as illustrated in FIGS. 2A and 2B is similar to the system 100a in the previous embodiment illustrated in FIG. 1, except that the system 100b further comprises a charged particle beam assembly 130 and an examination assembly 140, and the chamber 110b of the system 100b may further comprise a moving module 118.

In the present embodiment, the charged particle beam assembly 130 is capable of projecting a charged particle beam 132, and the focus of the second mirror 126 is far away from a position that the substrate 200 is projected by the charged particle beam 132, wherein the charged particle beam assembly 130 may be a scanning electron microscope (SEM) and the charged particle beam 132 may be an electron beam, but the charged particle beam assembly 130 is not limited to the SEM. In addition, the moving module 118 may be a lead screw and serving a lead screw driven table with the stage 114, such that the moving module 118 is capable of moving the substrate 200 by driving the stage 114. In addition, the portion 210 of the substrate 200 may have a circuit (not shown) and the circuit may have some leakage defects 220 (only one leakage defect 220 is illustrated in FIGS. 2A and 2B). Furthermore, the examination assembly 140 may be disposed on the wall 112, electrically connected to the light source 120 and capable of examining the leakage defects 220 of the substrate 200. Therefore, users may identify each leakage defect 220 as a short defect insensitive to the temperature or a junction defect sensitive to the temperature on the substrate 200 by using the system 100b.

In more detail, users may identify each leakage defect 220 as a short defect or a junction defect by processing the following steps. After the substrate 200 is held on the stage 114, users may locate the substrate 200 along a transmission path of the charged particle beam 132 as illustrated in FIG. 2A by using the moving module 118 first. Next, users may control the charged particle beam assembly 130 to project the charged particle beam 132 to scan the portion 210 by using the examination assembly 140 in a vacuum environment. Therefore, at least one leakage defect 220 on the substrate 200 may be found.

Thereafter, users may move the substrate 200 to locate a portion 210 of the substrate 200 close to the focus of the second mirror 126 as shown in FIG. 2B by using the moving module 118. Next, users may control the light beam 128 emitted from the lamp 122 to project on the portion 210 so as to heat the leakage defects 220 in the portion 210. After termination of light beam projection, users may identify the leakage defects 220 of the portion 210 by using the examination assembly 140.

In more detail, according to the semiconductor physics, the resistance of short defect is essentially independent on temperature but the resistance of junction leakage is clearly dependent on temperature. Besides, a gray-level of the leakage defects 220 is essentially proportional to the resistance of the leakage defects 220. Therefore, each leakage defect 220 in the portion 210 may be identified as a short defect or a junction defect by examining an examination result, for example a gray-level photo, of the portion 210, since the short defect is insensitive to the temperature and the junction defect is sensitive to the temperature.

Figure 3A:
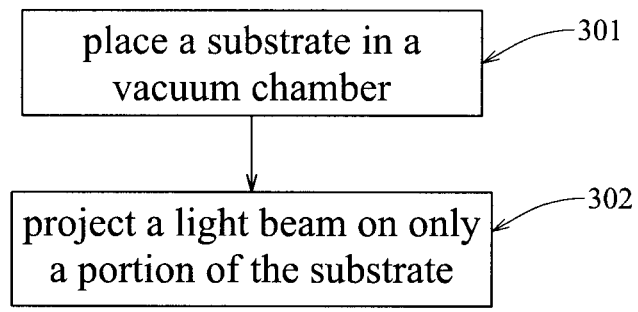
FIG. 3A is a flow chart of a method of heating a substrate in a vacuum environment according to an embodiment of the present invention.

FIG. 3A is a flow chart of a method of heating a substrate in a vacuum environment according to an embodiment of the present invention. However, the method of heating the substrate in a vacuum environment of the present invention should not be limited by using the system illustrated in above embodiments. In details, referring to FIG. 3A, any un-illustrated system able to process the following steps may be used.

First, a substrate is placed in a vacuumed chamber (301). Thereafter, a light beam emitted from a light source is projected on only a portion of the substrate, such that the portion is significantly heated before the whole substrate is heated (302).

Figure 3B:
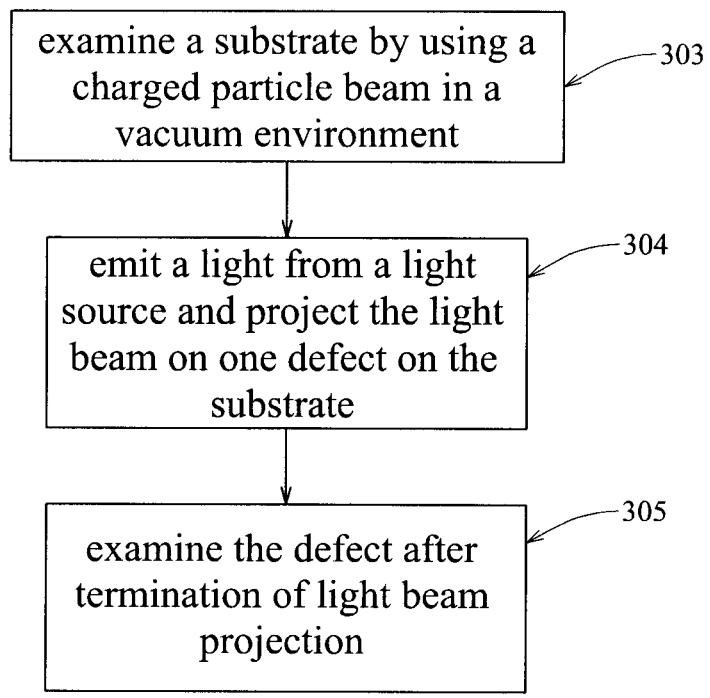
FIG. 3B is a flow chart of a method for identifying defects on a substrate according to an embodiment of the present invention.

FIG. 3B is a flow chart of a method for identifying defects on a substrate according to an embodiment of the present invention. Furthermore, the method of identifying the defects on the substrate of the present invention should not be limited by using the system illustrated in above embodiments, too. In details, referring to FIG. 3B, any un-illustrated system able to process the following steps may be used. First, a substrate is examined by using a charged particle beam in a vacuum environment (303), wherein at least one defect is located on the substrate. Thereafter, a light beam emitted from a light source is projected on at least one specific defect (304). Next, the specific defect is examined after termination of light beam projection (305), such that the specific defect is identified by the examination result.

Note that in experiment, the tester find that if using a heater located inside the chamber 110b where the substrate 200 is located to heat the substrate 200, the cost to eliminate the pollution, for example ion oscillations, induced by the heater is high. Hence, it is hard to identify the leakage defects 220 by watching how the gray-level of the leakage defects 220 is sensitive or insensitive to the temperature after the substrate 200 is heated and the heater is turn-off. Therefore, it is helpful to identify the leakage defects 220 by locating the light source 120 outside the chamber 110b to heat the leakage defects 220 of the portion 210.

However in other un-illustrated embodiments, the light source may be a laser or a combination of radiation lamps and lasers. In addition, the light source may use at least one optical element located outside the chamber to focus the light beam on the portion of the substrate, wherein the optical element may be a mirror as described in the above-mentioned embodiment, lens or a combination of mirrors and lenses.

Figure 4A:
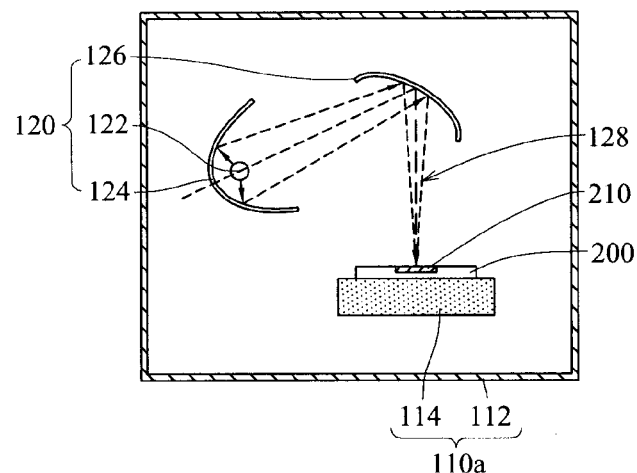
FIG. 4A is a schematic view of a system for heating a substrate in a vacuum environment according to another embodiment of the present invention.
Figure 4B:
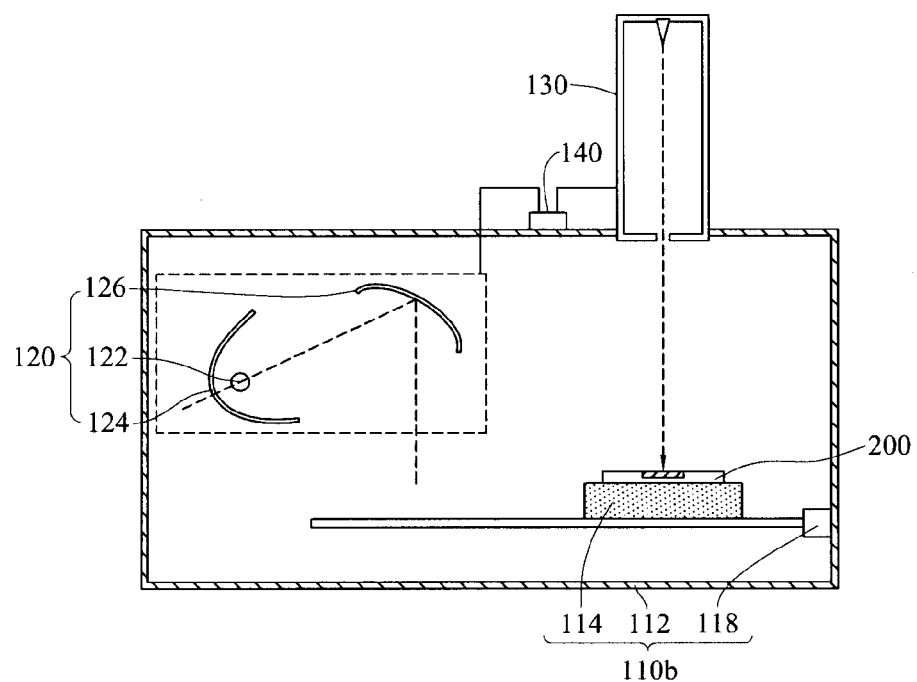
FIG. 4B is a schematic view of inspecting a substrate by using a system according to another embodiment of the present invention.

FIG. 4A is a schematic view of a system for heating a substrate in a vacuum environment according to another embodiment of the present invention. FIG. 4B is a schematic view of inspecting a substrate by using a system according to another embodiment of the present invention. In addition, referring to FIGS. 4A and 4B, the light source 120 may also be located inside the wall 112 of the chamber 110a, 110b if the pollution induced by the light source 120 is low.

Furthermore, whole light source 120 may be located outside the wall 112 as illustrated in the previous embodiments. However in other un-illustrated embodiments, a power portion of the light source may be located outside the vacuum environment and a luminescence portion of the light source may be located outside the vacuum environment. In addition, the system may have no moving module, and the configuration of the light source is adjusted, such that the focus of the second mirror is located on the portion of the substrate while the substrate is located on the position to be projected by the charged particle beam.

In summary, only a portion of a substrate is heated in a vacuum environment by using the method or the system of the present invention. Furthermore, defects on a substrate may be identified by using the method or the system of the present invention.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method of identifying defects on a substrate, comprising:
    examining a substrate by using a charged particle beam in a vacuum environment to obtain a first result, wherein at least one defect is located on said substrate;
    heating the defect with a light beam emitted from a light source;
    re-examining the defect using the charged particle beam in the vacuum environment after heating with the light beam to obtain a second result; and
    classifying the defect by comparing the first result and the second result.

2. The method as claimed in claim 1, wherein said light source is located outside said vacuum environment.

3. The method as claimed in claim 1, wherein a power portion of said light source is located outside said vacuum environment and a luminescence portion of said light source is located inside said vacuum environment.

4. The method as claimed in claim 1, wherein said defect is a leakage defect.

5. The method as claimed in claim 4, wherein said first result of said classifying step is a gray level, and said second result of said classifying step is a gray-level.

6. The method as claimed in claim 5, wherein said classifying step further comprises identifying said defect as a short defect when said second result is the same as said first result.

7. The method as claimed in claim 5, wherein said classifying step further comprises identifying said defect as a junction leakage when said second result differs from said first result.

8. The method as claimed in claim 1, further comprising using at least one optical element to focus said light beam on said defect, said optical element being chosen from a group consisting of the following: lens, mirror or combination thereof.

9. The method as claimed in claim 1, wherein said light source is chosen from a group consisting of the following: radiation lamp, laser or combination thereof.

10. The method as claimed in claim 1, wherein said charged particle beam is an electron beam.

11. A system for identifying defects by using a charged particle beam, comprising
    a chamber, holding a substrate in a vacuum environment;
    a charged particle beam assembly, projecting a charged particle beam on said substrate;
    a light source, projecting a light beam on at least a portion of said substrate; and
    an examination assembly,
    wherein at least one defect on the substrate is examined with the charged particle beam assembly within the vacuum environment to obtain a first result, heated with the light beam, re-examined in the vacuum environment with the charged particle beam assembly after heating with the light beam to obtain a second result, and classified by comparing the first result and the second result.

12. The system as claimed in claim 11, wherein said light source is located outside said vacuum environment.

13. The system as claimed in claim 11, wherein a power portion of said light source is located outside said vacuum environment and a luminescence portion of said light source is located inside said vacuum environment.

14. The system as claimed in claim 11, wherein said defect is a leakage defect.

15. The system as claimed in claim 14, wherein said first result is a gray level, and said second result is a gray-level.

16. The system as claimed in claim 15, wherein said defect is classified as a short defect when said second result is the same as said first result.

17. The system as claimed in claim 15, wherein said defect is identified as a junction leakage when said second result differs from said first result.

18. The system as claimed in claim 11, wherein said light source is chosen from a group consisting of the following: radiation lamp, laser or combination thereof.

19. The system as claimed in claim 11, said light source comprising a lamp, a first mirror and a second mirror, said lamp being located close to a proximal focus of said first mirror, said second mirror being located close to a distal focus of said first mirror, and said second mirror having a final focus located within said chamber.

20. The system as claimed in claim 19, the configuration of said light source being adjusted such that said final focus is located on said defect when said substrate is positioned where said defect was examined with said charged particle beam assembly.

21. The system as claimed in claim 19, further comprising a moving module for moving said substrate away from said charged particle beam and to said final focus.

22. The system as claimed in claim 11, wherein said charged particle beam is an electron beam.

23. The method as claimed in claim 1, further comprising:
moving said substrate to a final focus of said light beam with a moving module, after said examining step and before said heating step; and
returning said substrate from the final focus with the moving module, after said heating step and before said re-examining step.

* * * * *